United States Patent [19]
Koscher et al.

[11] Patent Number: 5,527,339
[45] Date of Patent: Jun. 18, 1996

[54] SURGICAL INSTRUMENT

[76] Inventors: Stefan Koscher, Lachstrasse 53; Johann Wuertz, Semmelweiss-Strasse 32, both of D-78459 Spaichingen, Germany

[21] Appl. No.: 273,990

[22] Filed: Jul. 12, 1994

[30] Foreign Application Priority Data

Sep. 24, 1993 [DE] Germany .................... 43 32 497.5

[51] Int. Cl.⁶ .................................................. A61B 17/32
[52] U.S. Cl. ............................ 606/205; 606/52; 606/207
[58] Field of Search .......................... 606/205–208, 606/51, 52

[56] References Cited

U.S. PATENT DOCUMENTS

| | | | |
|---|---|---|---|
| 2,113,246 | 4/1938 | Wappler | 606/205 |
| 5,176,702 | 1/1993 | Bales et al. | 606/208 |
| 5,263,967 | 11/1993 | Lyons, III et al. | 606/208 X |
| 5,282,800 | 2/1994 | Foshee et al. | 606/208 X |
| 5,308,358 | 5/1994 | Bond et al. | 606/207 X |
| 5,336,238 | 8/1994 | Holmes et al. | 606/208 |
| 5,342,391 | 8/1994 | Foshee et al. | 606/52 |
| 5,368,606 | 11/1994 | Marlow et al. | 606/207 |

*Primary Examiner*—Stephen C. Pellegrino
*Assistant Examiner*—Michael Peffley
*Attorney, Agent, or Firm*—Bachman & LaPointe

[57] ABSTRACT

A surgical instrument with two elements sliding into one another has at least one jaw part connected with a sliding element. Both elements are connected with one another detachably by means of a catch device. A distance between the end of a sliding element and the jaw part is variable, but is invariable when at least one jaw part is fixed.

10 Claims, 1 Drawing Sheet

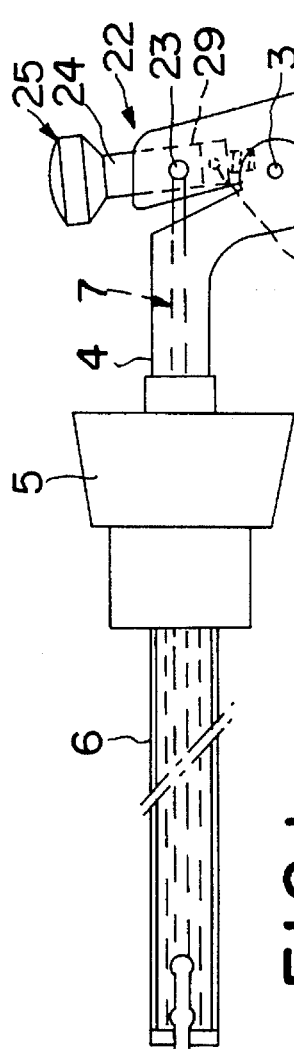
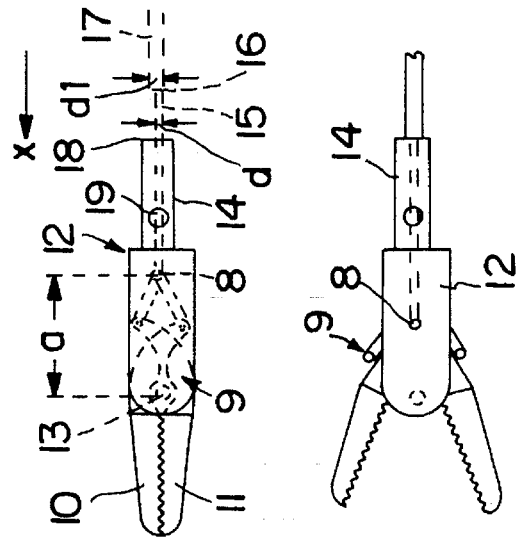
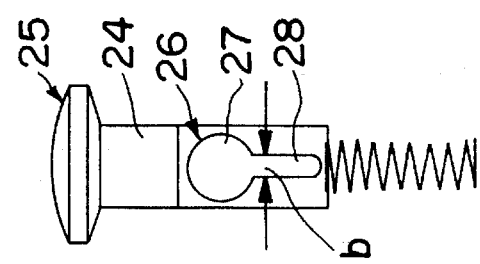
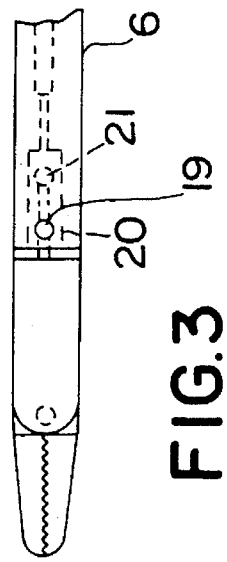
FIG.1
FIG.2
FIG.3
FIG.4

SURGICAL INSTRUMENT

BACKGROUND OF THE INVENTION

The invention concerns a surgical instrument with two elements sliding into one another, at least one jaw part being connected with a sliding element.

Surgical instruments are known in diverse shapes and designs. The present invention refers to a surgical instrument, by means of which at least one jaw part may be moved vis-a-vis another jaw part. The jaw parts may include cutters, tongs, clamps, pincers, or the like.

In this case at the present time with the increasing demands for hygiene, for example as a result of the possibilities for transmission of the AIDS virus, it is mandatory that surgical instruments can be disassembled into their individual parts and cleaned in a simple way. Only in this way can the cleaning medium reach the individual elements and have its maximum effect.

An instrument capable of being disassembled is known, for example, from EP A- 0 513 471. There at least one jaw part is connected with a pulling element, the jaw part being moved interacting with a surrounding tube, but it may be removed from the tube together with the pulling element.

SUMMARY OF THE INVENTION

The task of the present invention is to create a surgical element of the above-mentioned type, in the case of which it is easy to loosen the jaw parts together with the corresponding elements from the other elements, but the opening, and closing no longer depends on the other element.

The fact that both elements are connected with one another detachably via a catch device, and that the distance between the end of one sliding element and the jaw part is variable, but is made invariable by means of fastening at least one jaw part, leads to the solution of this task.

This arrangement has the considerable advantage that in the case of normal operation of the surgical instrument in the working position the two elements remain connected to one another, but that at least one jaw part can be moved by means of relative movement of one element with respect to the other element. In this case preferably the movement of the jaw part does not depend on the interaction of the two elements movable relative to one another, but a sliding element is connected with at least one jaw part via a corresponding opening, and closing mechanism.

In this case the arrangement is chosen so that in the case of undisturbed motion of the jaw parts the two elements remain in the resting position, and that, if a jaw part is fastened, that is, the distance between the end of one sliding element and the jaw part is fixed, the two elements extend out of their resting position. The two elements can be separated from one another in this simple way.

BRIEF DESCRIPTION OF THE DRAWINGS

Further advantages, features, and details of the invention result from the following description of preferred specific embodiments as well as by means of the drawings, wherein:

FIG. 1 shows a top view of a disassembled partially shown surgical instrument in accordance with the invention;

FIG. 2 shows a top view of a surgical instrument shown in FIG. 1 with the jaws in the open position;

FIG. 3 shows a top view of the jaw area of the surgical instrument shown in FIG. 1 with the jaws in the closed position and in the operating position of the instrument; and FIG. 4 shows a top view of part of a holder for the surgical instrument shown in FIG. 1.

DETAILED DESCRIPTION OF PREFERRED EMBODIMENTS

Preferably the present device uses an opening and closing mechanism which connects a hinge on one sliding element with a pivot for at least one jaw part. Preferably this is a matter of a known bent lever, to which, however, the invention is not to be limited. It is essential only that in the operating position the distance between the hinge and the pivot is variable, but that when the jaw part is fastened, this distance also is fixed and thus when force is exerted on one movable element it is removed from its catch position.

Preferably the pivot is located within a jaw holder, by means of which a catch connection is made with the other element. However it is also conceivable that the pivot itself forms one part of the catch device. For example, the pivot may be made as a catch pin, which engages into the corresponding catch depression of a surrounding tube.

Preferably a pulling and pushing element and a surrounding tube are chosen as the elements sliding into one another. The opening and closing mechanism could be attached to the tube via the above mentioned hinge, however as a rule the reverse arrangement is chosen. In this case, the opening and closing mechanism together with at least one jaw part is located on the pulling and pushing element. For example the latter may be made as a rod or wire.

The motion of the pulling and pushing element within the tube, may be made via any drive. If a manual drive is chosen, the tube is connected with a handle of the tongs and the pulling and pushing element is detachably connected with a further handle of the tongs via a holder. Both handles of the tongs again have a common hinge. This is one of the more usual configurations of a hand instrument, to which, however, the invention is not to be limited.

Different possibilities also are conceivable for the catch connection between the jaw holder the opening and the closing mechanism, and the tube. For example, the jaw holder could have a ring collar which engages in a corresponding ring channel within the tube.

In a preferred embodiment the jaw holder has catch pins which engage in catch depressions in the tube.

Also the detachable attachment of the pulling and pushing element on the handle of the tongs is to be improved. In this case a push button, which has a hollow shaft, is located in the handle. The hollow shaft has a hole, which can receive a ball which is molded to the end of the pulling and pushing element. A slot through which the pulling and pushing element passes, is adjacent to this hole. Only when the push button is operated does the ball enter the area of the hole and is able to slide out of the hole.

The advantage of the present invention consists in the fact that the jaw parts together with the jaw holder and the pulling and pushing element, as well as the opening and closing mechanism may be removed from the tube simply, and that the jaw parts may be fastened, for example, in the closed position. In this way the distance between the above mentioned hinge and the jaw parts no longer changes so that the holder is pushed out of the tube. Now it is necessary only to operate the push button,- by means of which the ball is released.

This instrument in accordance with the invention is designed extremely simply, and is extremely simple to operate so that nothing stands in the way of frequent and thorough cleaning. Further in this way very different jaw parts may be connected with only one tube and a handle of the tongs. The tube and the handles then form a basic element with which a great range of jaw parts may be associated.

Referring to the drawings, a surgical instrument, as shown in FIG. 1, has a handle 1 and a handle 2, which are connected with one another by means of a hinge 3. On the other side of hinge 3, a tube section 4 connects to the handle 1, which tube section in the present embodiment is connected to a tube 6 via a rotating unit 5, which, however, is not essential to the invention.

The pulling and pushing element, 7, which at one end is hinged and connected detachably with a handle 2, and on the other end with an opening and closing mechanism 9 for jaw parts 10 and 11 via a hinge 8, passes through the tube 6 and in the present embodiment, also the tube section 4. The opening and closing mechanism 9 is located in a jaw holder 12, in which there is a pivot 13, around which the jaw parts 10 and 11 turn.

In the case of shifting the pulling and pushing element, which in the present specific embodiment is made as a push rod 7, in the direction x, the hinge 8 is pushed to the pivot 13 and thus moves a distance a, the opening and closing mechanism 9 being expanded, as is shown in FIG. 2. In this way the jaw parts 10 and 11 are opened. Of course closing the jaw parts 10 and 11 may be performed by means of a correspondingly reversed arrangement.

A sleeve 14, through which a part 15 of the push rod 7 with a diameter d passes, is connected to the rear of the jaw holder 12. A main part 17 of the push rod 7 with a diameter $d^1$, which is greater than the diameter d of the part 15, follows behind a ring collar 16.

Between the ring collar 16 and the edge 18 of the sleeve 14 there is a distance which is reduced during the motion of the pushing element 7 in the direction A, as is the distance, until the ring collar strikes the outside edge 18. This also is shown in FIG. 2.

The sleeve 14, and thus also the jaw holder 12, may be connected with the tube 6 via a catch arrangement. In the present embodiment, this catch arrangement consists of two catch pins, which project from the sleeve 14 on both sides. In the operating position, as is shown in FIG. 3, these catch pins 19 engage in catch depressions 20, which are provided in the tube 6 in a longitudinal slot 21.

At the other end, after passing through the tube 6, push rod is connected detachably with a holder 22. In a simple specific embodiment, the push rod 7 has a ball on one end, which rests in a shaft 24 of a push button 25. The shaft 24 has an opening 26, which is shown in FIG. 4 in greater detail, for the push rod 7. For receiving the ball 23, the opening 26 has an approximately circular hole 27, which is adjacent to a slot 28 below. Thus the ball 23 may be pushed through the hole 27 into the shaft 24 of the push button 25 and then engages the slot 28. Thus the slot 28 has a width b which is approximately larger than the diameter $d^1$ of the push rod 7.

In addition, the holder 22 is held in a corresponding guide recess 29 in the handle 2 on the other side of the hinge 3 and is supported below by a spring 30.

The mode of operation of the surgical instrument invented is as follows:

In the operating position, the catch pins 19 engage in the catch recess 20. This provides for secure holding when using the surgical instrument, that is during the opening and closing of the jaw parts 10 and 11, since the push rod is able to move unhindered in the direction x during the opening and closing of the handles 1 and 2. In this case, the distance between the ring collar 16 and the outer edge 18 of the sleeve 14 decreases or increases. The hinge 8 can approach or recede from the pivot 13 unhindered and thus reactivate the opening and closing mechanism.

If the jaw parts, the jaw holder, the opening, closing mechanism, and the push rod are to be removed from the tube 6, the jaw parts 10 and 11 are held in the closed position. This means that the hinge 8 no longer can approach the pivot 13. Now if the handles 1 and 2 are moved, the push rod 7 pushes the jaw holder 12 with the sleeve 14 and the catch pin 19 out of the tube 6 and the catch recess 20. Thus the jaw holder is released so that the push rod now only has to be released from the holder 22. For this the handles 1 and 2 are opened as far as possible and the push button 25 is operated. The ball 23 enters the area of the hole 27 of the opening 26 and may slide out of the hole 27. The push rod 7 with all jaw elements may be removed from the tube 6 and the elements may be cleaned.

In reassembling the surgical instrument, the push rod 7 is reinserted into the tube 6, the handles 1 and 2 are opened, and the push button 25 is moved against the spring 30. The hole 27 comes into the receiving position for the ball 23, which slides into the opening 26. Upon releasing the push button 25 the ball 23 slides behind the slot 28. If the handles 1 and 2 now are closed, the sleeve 14 together with the catch pin 19 is drawn into the tube 6 so that the catch pins 19 may engage in the catch recesses 20. Now the surgical instrument is in the operating position.

If necessary the tube 6 may be coating with an insulating layer or an insulating casing.

We claim:

1. A surgical instrument which comprises: first and second elements in sliding relationship with each other, at least said first element having an end, wherein the first element is a pulling and pushing element and the second element is a tube and the first element is located at least in part in said tube; movable jaw parts spaced a distance from the end of said first element, with at least one jaw part connected to said first element by connecting means; a catch device detachably connecting said elements with one another and permitting removal of the first element from the second element; wherein, the distance between the end of the first element and the jaw parts being variable, but being invariable when said jaw parts are fixed, and wherein the connection between the first and second elements by the catch device is released by fixing said jaw as to allow sliding the first element when said jaw parts are fixed.

2. An instrument according to claim 1, wherein the first element is connected to the jaw parts by means of an opening and closing mechanism.

3. An instrument according to claim 2, wherein the first element includes a hinge, and wherein the jaw parts include a pivot, with the opening and closing mechanism connecting said hinge with said pivot.

4. An instrument according to claim 3, wherein the pivot is located in a jaw holding means.

5. An instrument according to claim 4, wherein the tube is connected detachably with a handle and the first element is connected detachably with a further handle by means of a holder, both of said handles being connected with one another by means of a second hinge.

6. An instrument according to claim 5, wherein the jaw holding means is connected with the first element via said pivot, the opening and closing mechanism, and the hinge, and wherein the jaw holding means is operatively engaged with the tube via a releasable catch connection.

7. An instrument according to claim 6, including catch pins on the jaw holding means which engage in catch depressions in the tube.

8. An instrument according to claim 7, wherein the holder has a hole with a changeable position for receiving a ball, said ball being molded on the end of the first element.

9. An instrument according to claim 8, including a slot with a larger width than the diameter of the first element located adjacent to the hole, the opening of the hole being connected to a push button.

10. An instrument according to claim 9, wherein the push button is connected to a guide recess in the further handle and is guided against the pressure of a spring.

* * * * *